(12) United States Patent
Balji et al.

(10) Patent No.: US 8,396,537 B2
(45) Date of Patent: Mar. 12, 2013

(54) METHOD AND SYSTEM TO MEASURE ECG AND RESPIRATION

(75) Inventors: Jack Balji, Mahwah, NJ (US); Cadathur Rajagopalan, Dumont, NJ (US)

(73) Assignee: Mindray DS USA, Inc., Mahwah, NJ (US)

( * ) Notice: Subject to any disclaimer, the term of this patent is extended or adjusted under 35 U.S.C. 154(b) by 635 days.

(21) Appl. No.: 12/426,834

(22) Filed: Apr. 20, 2009

(65) Prior Publication Data

US 2010/0268093 A1     Oct. 21, 2010

(51) Int. Cl.
*A61B 5/04*     (2006.01)
(52) U.S. Cl. ....................................................... 600/509
(58) Field of Classification Search .................... 600/509
See application file for complete search history.

(56) References Cited

U.S. PATENT DOCUMENTS

| | | | | |
|---|---|---|---|---|
| 5,189,609 | A * | 2/1993 | Tivig et al. | 600/300 |
| 5,983,127 | A | 11/1999 | dePinto | |
| 6,047,203 | A * | 4/2000 | Sackner et al. | 600/388 |
| 7,184,817 | B2 * | 2/2007 | Zhu et al. | 600/513 |
| 7,277,752 | B2 * | 10/2007 | Matos | 607/5 |

OTHER PUBLICATIONS

Q Li, et al., "Robust heart rate estimation from multiple asynchronous noisy sources using signal quality indices and a Kalman filter," IOP Publishing, Physiol. Meas. 29 (2008), pp. 15-32.
Q Li, et al., "Artificial arterial blood pressure artifact models and an evaluation of a robust blood pressure and heart rate estimator," Bio Med Eng Online, 2008 (in submission).

* cited by examiner

*Primary Examiner* — Christopher D Koharski
*Assistant Examiner* — Nadia Ahmad
(74) *Attorney, Agent, or Firm* — Kory D. Christensen; Stoel Rives LLP (57) ABSTRACT

A method for monitoring the respiration rate of a patient includes attaching a plurality of electrocardiogram (ECG) electrodes and a pressure sensor to a patient, producing a first respiration signal based on variations detected in signals provided by the ECG electrodes attached to the patient, and producing a second respiration signal based on pressure variations detected in the pressure sensor secured to the patient. The method also includes selecting at least one of the first respiration signal and the second respiration signal based on respective signal qualities and producing a respiration rate from the selected signal. The method also includes providing indicia of the respiration rate. The method may also include displaying ECG signals with the indicia of the respiration rate.

22 Claims, 5 Drawing Sheets

METHOD AND SYSTEM TO MEASURE ECG AND RESPIRATION

TECHNICAL FIELD

This disclosure generally relates to patient monitoring. In particular, this disclosure relates to simultaneously monitoring a patient's heart and respiratory rate.

SUMMARY

Systems and methods are provided for monitoring electrocardiogram (ECG) signals and respiration rates.

In one embodiment, a method for monitoring a respiration rate of a patient includes attaching a plurality of ECG electrodes and a pressure sensor to a patient, producing a first respiration signal based on variations detected in signals provided by the ECG electrodes attached to the patient, and producing a second respiration signal based on pressure variations detected in the pressure sensor secured to the patient. The method also includes selecting at least one of the first respiration signal and the second respiration signal based on respective signal qualities and producing a respiration rate from the selected signal. The method also includes providing indicia of the respiration rate. In certain embodiments, the method may also include displaying ECG signals with the indicia of the respiration rate.

In another embodiment, an integrated apparatus for measuring electrical signals and physical movements in a patient includes a body with a top surface and a bottom surface, an adhesive covering at least a portion of the bottom surface to temporarily secure the integrated apparatus to the patient's skin, and an electrically conductive lead attachment passing from the top surface to the bottom surface of the body to provide electrical communication between the patient's skin and an electrocardiogram (ECG) lead. The integrated apparatus also includes a pressure capsule secured below the top surface of the body. The pressure capsule is responsive to changes in pressure applied thereto. The integrated apparatus also includes a pressure communication tube connected to the pressure capsule to communicate pressure variations within the pressure capsule to a pressure transducer.

Additional aspects and advantages will be apparent from the following detailed description of preferred embodiments, which proceeds with reference to the accompanying drawings.

DETAILED DESCRIPTION

Generally, patient monitoring may include monitoring the status of a patient's heart using electrocardiogram (ECG) signals and the patient's respiratory rate. Electrical waves cause the heart muscle to pump. These electrical potentials can be sensed using electrodes attached to a patient's skin. Electrodes on different sides of the heart measure the activity of different parts of the heart muscle. An ECG displays voltages between pairs of electrodes (leads) from different directions. Thus, an ECG may be used to discern overall rhythm of the heart and problems, if any, in different parts of the heart muscle.

Several techniques may be used to obtain a respiration signal from ECG leads. For example, beat-to-beat variations may be observed in RR intervals in an ECG signal, which may be due to respiratory sinus arrhythmia. Another technique may include deriving a respiration rate by computing the ratio of the areas of QRS complexes in two different leads or assessing direction changes of successive vectocardiogram loops.

Another common technique is to measure a thoracic impedance signal using ECG electrodes. This method determines the patient's respiration rate based on an impedance measurement that is separate from the ECG signal. Thoracic impedance respiration monitoring includes injecting a high frequency current into the ECG electrodes, and measuring the changes in impedance due to respiration. The changes in impedance due to respiration, however, are small compared to a base impedance. For example, a normal base impedance may be between approximately 1 kOhm to approximately 2 kOhms. Whereas, the change in impedance due to respiration may be on the order of only approximately 0.5 Ohms to approximately 1 Ohm. Further, changes in impedance due to artifact (e.g., patient movement, crying, and/or feeding) are very large and may have the same order of amplitude as the signal of interest. Thus, thoracic impedance respiration monitoring is difficult to use for children or infants. In addition, the high frequency current injected may interfere with certain types of pacemakers and non-invasive cardiac output measurements that use a bio-impedance technique. Further, impedance changes due to cardiac activity may, at times, be mistakenly detected as respiration.

Thus, in certain embodiments disclosed herein, a respiration rate is monitored using signals obtained through ECG electrodes and a pressure sensor attached to a patient's body. In one embodiment, ECG signals are acquired via silver/silver chloride electrodes attached to the body. The ECG signals may be printed or displayed to monitor the patient's heart rhythm and/or to identify weakness in different parts of the heart muscle. The ECG electrodes may also be used to produce an "ECG respiration signal" that represents the patient's respiration rate. As discussed above, the ECG respiration signal may be based on analysis of the ECG signal. In another embodiment, the ECG electrodes are used to generate the ECG respiration signal using thoracic impedance respiration monitoring.

The pressure sensor is used to produce a "pressure respiration signal." For example, a pressure capsule or strain gauge may be secured to the patient's abdomen. Pressure changes in the pressure capsule or strain gauge are associated with the movement of the abdomen during breathing. Thus, pressure changes in the pressure capsule or strain gauge are used to derive a respiration rate.

In one embodiment, one or more pressure sensors are placed under one or more of the ECG electrodes. For example, a pressure sensor may be secured to a patient by an ECG electrode placed on a lower part of the abdomen to detect respiratory movements of the abdomen. The pressure sensor may be secured to the patient by an ECG electrode that is large enough to hold the pressure sensor in place while making sufficient electrical contact with the patient's skin so as to measure ECG signals and/or thoracic impedance signals. This may be accomplished using a large single electrode patch where the pressure sensor does not block the electrical connection between the electrode and the patient's skin, or a multiple electrode patch where the pressure sensor is secured to the patient while at least one of the electrodes in the patch continues to provide an electrical connection to the patient's skin.

In another embodiment, an integrated apparatus is attached to the patient that measures both electrical signals and physical movements (e.g., pressure changes due to respiration). The integrated apparatus includes both a pressure sensor and an electrode that may be attached to an ECG lead. Thus, the integrated apparatus may be used to obtain both a pressure respiration signal and an ECG respiration signal.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions.

Figure 1A:
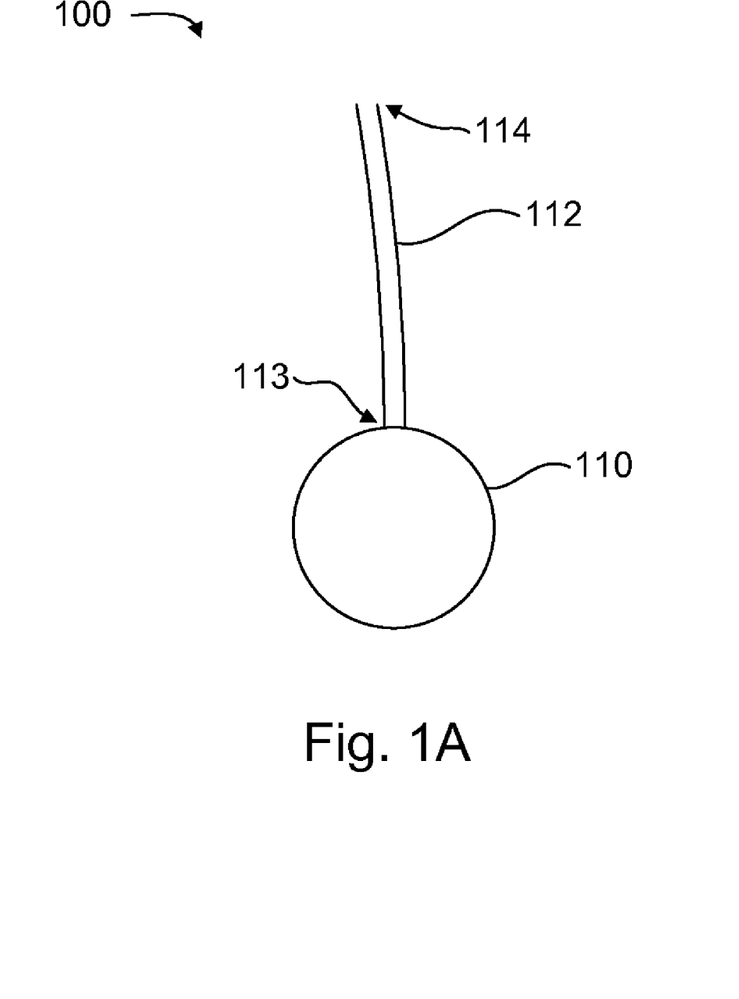
FIG. 1A is a top view of a pressure sensor for measuring respiration according to one embodiment.
Figure 1B:
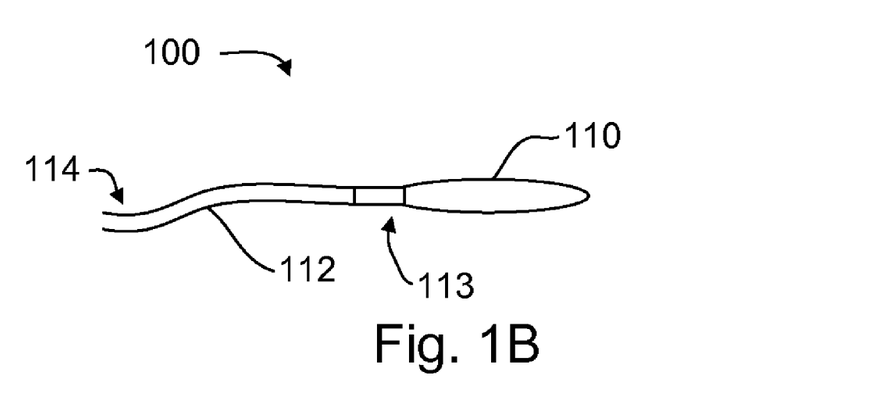
FIG. 1B is a side view of the pressure sensor shown in FIG. 1A according to one embodiment.

FIG. 1A is a top view of a pressure sensor 100, and FIG. 1B is a side view of the pressure sensor 100 used to acquire a pressure respiration signal according to one embodiment. The pressure sensor 100 includes a pressure capsule 110 and a pressure communication tube 112. The pressure capsule 110 may include a hollow bladder or balloon. In one embodiment, the pressure capsule 110 has a diameter of approximately 18 millimeters and a height of approximately 4 millimeters. An artisan will understand from the disclosure herein, however, that these measurements are provided by way of example only and that the pressure capsule 110 may be substantially smaller or substantially larger depending on the particular application. Suitable pressure capsules 110 and pressure communication tubes 112 are available from Viomedix Limited of Gordon Road, Buxted, Uckfield, East Sussex TN22 4LH (UK).

In one embodiment, the pressure capsule 110 comprises a plastic material configured to respond to respiration movements when secured to a patient. For example, the pressure capsule 110 may be attached to the abdomen or chest of the patient, and breathing may cause the pressure inside the pressure capsule 110 to change. The plastic material of the pressure capsule 110 may be very thin, and the pressure capsule 110 may include therein a biasing element such as a sponge or other material to counteract the movement of the patient.

A proximal end 113 of the pressure communication tube 112 is connected to the pressure capsule 110. The pressure communication tube 112 is hollow and may include a plastic material. A distal end 114 of the pressure communication tube 112 is configured for connection, as discussed in detail below, to a pressure measurement channel of a patient monitor. For example, the distal end 114 of the pressure communication tube 112 may be connected to an invasive blood pressure port of the patient monitor.

In one embodiment, the pressure communication tube 112 includes a thicker plastic material than that used for the pressure capsule 110 such that pressures applied to the pressure communication tube 112 during normal operation do not substantially interfere with the pressure changes detected by the pressure capsule 110. The pressure within the pressure sensor 100 is based on the volume of air within both the pressure capsule 110 and the pressure communication tube 112. Thus, the pressure capsule 110 material is selected to be more sensitive to movements than the material of the pressure communication tube 112. Further, a longer pressure communication tube 112 may cause air pressure changes in the pressure capsule 110 to become less detectable. Thus, in certain embodiments, the length of the pressure communication tube 112 is selected so as to provide adequate sensing of pressure changes applied to the pressure capsule 110 during respiration.

When the pressure capsule 110 is held in place against the abdominal wall of a patient, abdominal movement during respiration results in compression and decompression of the pressure capsule 110. Compression and decompression of the pressure capsule 110 causes a pressure change inside the pressure capsule 100. These pressure changes are communicated to the pressure measurement channel of the monitor through the pressure communication tube 112. As discussed below, the pressure measurement channel of the monitor includes a pressure transducer that converts changes in pressure into an electrical signal. This pressure signal is representative of respiration (e.g., it is the pressure respiration signal), and may be used to derive a respiration rate and/or determine a cessation of breathing. In one embodiment, the patient monitor includes software modifications on the pressure channel to derive the respiration rate information.

Figure 2:
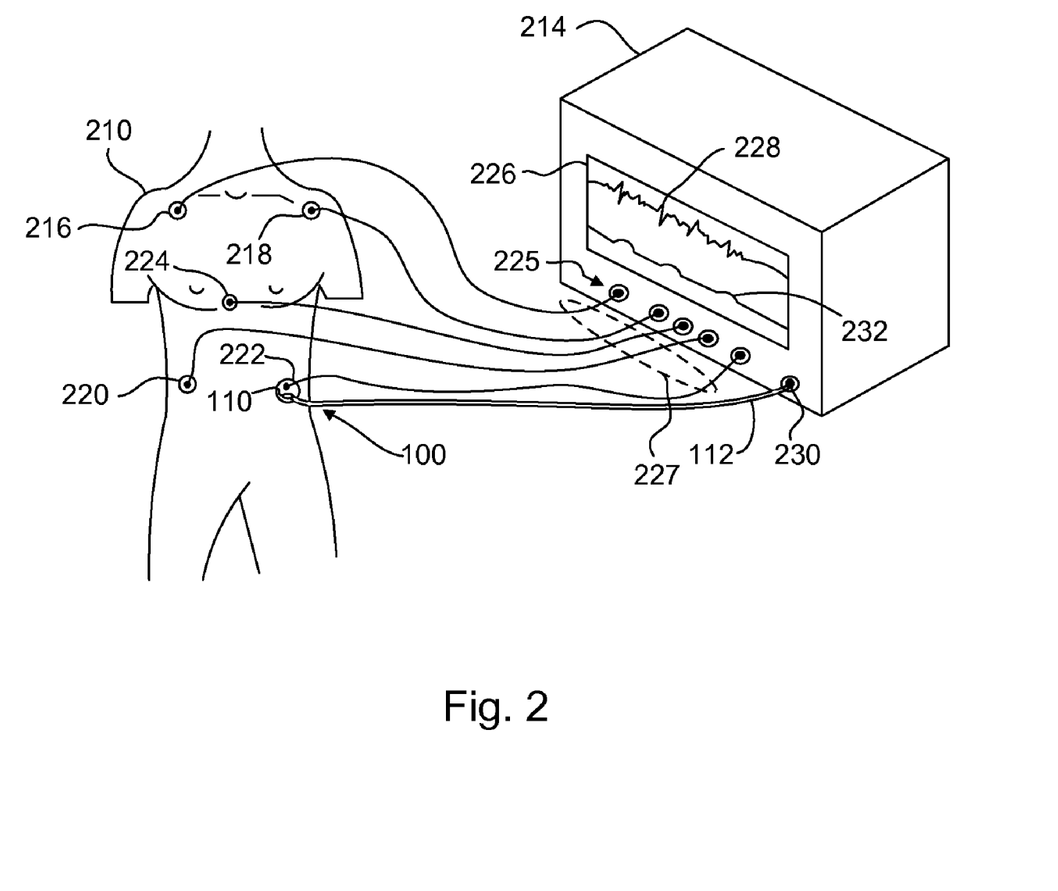
FIG. 2 graphically illustrates a patient connected to a patient monitor through a plurality of ECG electrodes according to one embodiment.

FIG. 2 graphically illustrates a patient 210 connected to a patient monitor 214 through a plurality of ECG electrodes 216, 218, 220, 222, 224 according to one embodiment. The ECG electrodes 216, 218, 220, 222, 224 are connected to respective ECG lead channels 225 (five shown) of the patient monitor 214 through respective ECG leads 227 (five shown).

The patient monitor 214 includes a display 226 for displaying an ECG signal 228 provided through the ECG leads 227. While the example shown in FIG. 2 illustrates a 5-lead arrangement, an artisan will recognize from the disclosure herein that other lead systems may also be used including, for example, a 12-lead system, a 6-lead system, or a 3-lead system.

As shown in FIG. 2, in one embodiment, one of the ECG electrodes 222 secures a pressure sensor 100 to the patient. For example, the pressure capsule 110 shown in FIGS. 1A and 1B may be placed under the electrode 222, or as discussed below, may be integrated as part of the electrode 222. In FIG. 2, the pressure capsule 110 is placed under or integrated with the ECG electrode 222 placed on the lower abdomen of the patient 210. However, an artisan will understand from the disclosure herein that the pressure capsule 110 may be placed under or integrated with a different ECG electrode 216, 218, 220, 222, 224, and/or that more than one pressure sensor 100 may be used.

The pressure communication tube 112 extends from the ECG electrode 222 to a pressure measurement channel 230 of the patient monitor 214. The pressure measurement channel 230 may include a pressure transducer (not shown) to convert pressure changes in the pressure sensor 100 to an electrical pressure respiration signal related to the patient's respiration rate.

In addition to providing measurements for the ECG signal 228, certain pairs of ECG electrodes (typically ECG electrodes 216 and 222, or 216 and 218) are also used to determine an ECG respiration signal related to the patient's respiration rate. As discussed in detail below, the patient monitor 214 analyzes the ECG respiration signal and the pressure respiration signal to determine the patient's respiration rate. The display 226 may display a waveform 232 representative of the determined respiration. The waveform 232 may include a sequence of times (represented by way of example in FIG. 2 as a series of peaks) at which the patient 210 breathes. In addition, or in other embodiments, the display 226 may display a numerical value (not shown) of the determined respiration rate.

Figure 3A:
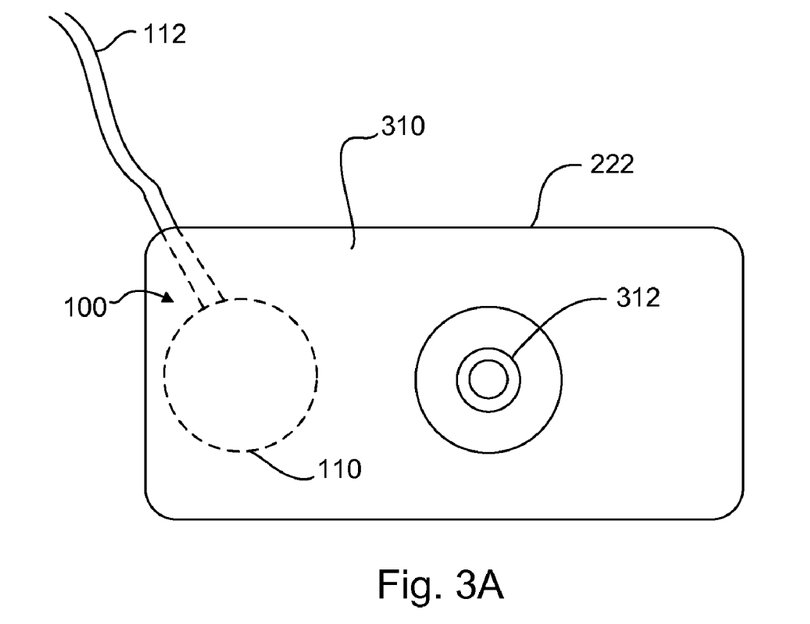
FIG. 3A schematically illustrates a top view of an adhesive ECG electrode with a pressure capsule secured thereunder according to one embodiment.
Figure 3B:
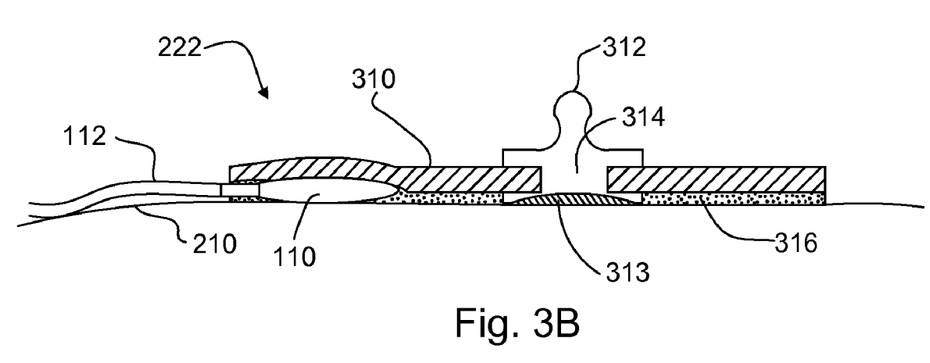
FIG. 3B is a side view of the ECG electrode shown in FIG. 3A according to one embodiment.

FIG. 3A schematically illustrates a top view of an adhesive ECG electrode 222 with the pressure capsule 110 placed thereunder according to one embodiment. FIG. 3B is a side view of the ECG electrode 222 with the pressure capsule 110 placed thereunder. The ECG electrode 222 may include a body 310, an electrically conductive lead attachment 312 passing through an insertion hole 314 in the body 310, an electrically conductive gel 313 for providing an electrical connection between the lead attachment 312 and the patient's body 210, and an adhesive 316 for attaching the ECG electrode 222 to the patient's body 210. As an artisan will understand from the disclosure herein, the adhesive 316 may be electrically conductive in certain embodiments to reduce the impedance of the ECG electrode. The lead attachment 312 is configured to connect to an ECG lead 227 for communicating ECG signals to the patient monitor 214. For illustrative purposes, FIG. 3B shows the pressure capsule 110 placed under the ECG electrode 222 so as to be secured by the body 310 and the adhesive 316 against the skin of the patient 210.

Figure 4A:
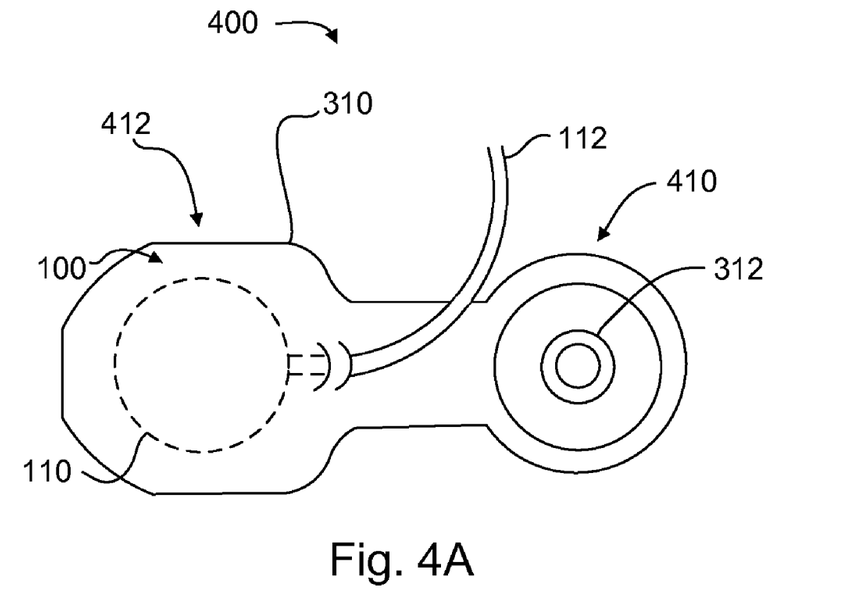
FIG. 4A illustrates a top view of an integrated apparatus for measuring electrical signals and physical movements in a patient according to one embodiment.
Figure 4B:
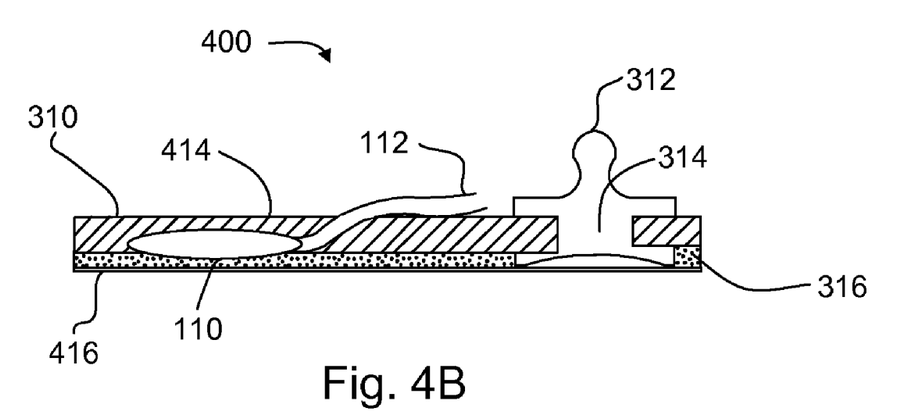
FIG. 4B is a side view of the integrated apparatus shown in FIG. 4A according to one embodiment.

In another embodiment, an ECG electrode and a pressure sensor are integrated into a single apparatus. For example, FIG. 4A illustrates a top view of an integrated apparatus 400 for measuring electrical signals and physical movements in a patient according to one embodiment. FIG. 4B is a side view of the integrated apparatus 400 according to one embodiment. The integrated apparatus 400 includes a body 310 comprising a flexible, non-electrically conducting material. The body 310 includes an ECG portion 410 and a pressure portion 412. The ECG portion 410 includes an electrically conductive lead attachment 312 passing through an insertion hole 314 in the body 310. As discussed above, the lead attachment 312 is configured to make electrical contact with the patient 210 (e.g., through an electrically conducting gel 313 shown in FIG. 3). The pressure portion 412 includes a pressure sensor 100. The pressure sensor 100 may include a pressure capsule 110 embedded under a top surface 414 of the body 310 and a pressure communication tube 112 that extends from the pressure capsule 110 through an opening in the top surface 414 of the body. The pressure capsule 110 may be glued or otherwise affixed to the body 310.

The integrated apparatus 400 includes an adhesive 316 for attaching the integrated apparatus 400 to the skin of the patient 210. As discussed above, in certain embodiments the adhesive 316 may be electrically conductive. The integrated apparatus 400 may also includes a peel off backing 416 that may be removed by the user to expose the adhesive 316 when the integrated apparatus 400 is attached to a patient 210.

As shown in FIG. 4A, the body 310 of the integrated apparatus 400 may be shaped so as to allow the user to apply the integrated apparatus 400 to the skin of the patient 210 with sufficient separation between the ECG portion 410 and the pressure portion 412 of the integrated apparatus 400. Thus, during use, the electrically conducting lead attachment 312 and the pressure capsule 110 are both properly secured to the patient 210, and the ECG leads 227 and pressure communication tube 112 do not interfere with each other. An artisan will understand from the disclosure herein, however, that the body 310 of the integrated apparatus 400 may have any shape. In certain embodiments, the integrated apparatus 400 is disposable.

Figure 5:
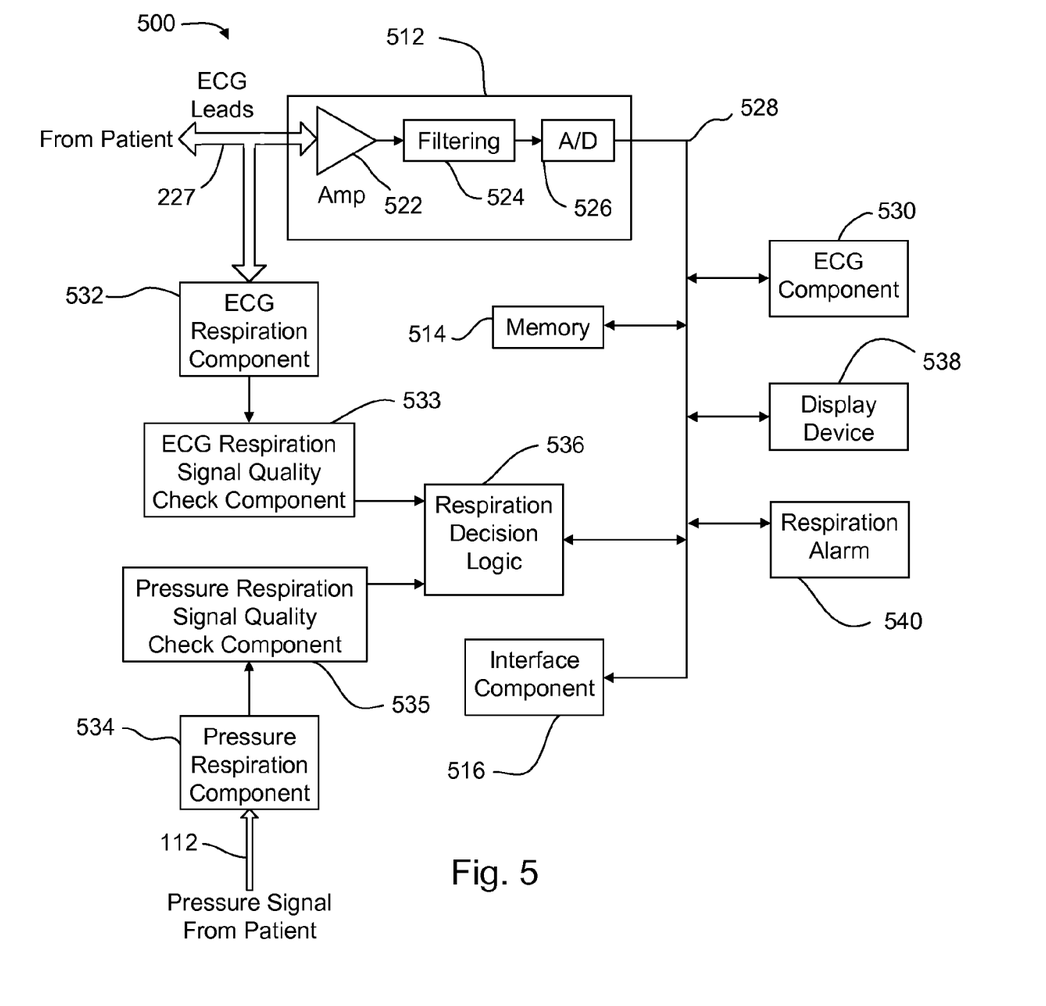
FIG. 5 is a simplified block diagram of a system for monitoring ECG signals and patient respiration according to one embodiment.

FIG. 5 is a simplified block diagram of a system 500 for monitoring ECG signals and patient respiration according to one embodiment. The system 500 includes a plurality of ECG leads 227 electrically connected to a receiver component 512 that is in communication with a memory device 514, an interface component 516, an ECG component 530, and a display device 538. The ECG leads 227 are configured to connect to respective ECG electrodes attached to a patient 210 (see FIG. 2) to detect ECG signals.

The receiver component 512 may include, for example, an amplification component 522 to amplify the ECG signals detected by the leads 227, a filtering component 524 to eliminate undesirable noise from the ECG signals, and an analog-to-digital (A/D) converter 526 to provide converted ECG signals through a system bus 528 to the memory device 514, the interface component 516, the ECG component 530, and the display device 538.

As shown in FIG. 5, the system 500 also includes an ECG respiration component 532 connected to the ECG leads 227. The ECG respiration component 532 produces an ECG respiration signal based on signals measured using the ECG leads 227. The ECG respiration component 532 provides the ECG respiration signal to an ECG respiration signal quality check component 533. The ECG respiration signal quality check component 533 runs a quality test on the ECG respiration signal. In one embodiment, the ECG respiration component 532 is configured to determine the thoracic impedance respiration of the patient. Those skilled in the art will recognize that the ECG respiration component 532 may determine the thoracic impedance respiration of the patient using known techniques including, for example, injecting a high frequency current into one of the ECG leads 227 and measuring the high frequency current detected on one or more of the other ECG leads 227. As discussed above, the ECG respiration component 532 in other embodiments may produce ECG respiration signals based on changes to ECG signals due to respiration.

The system 500 also includes a pressure respiration component 534 connected to the pressure communication tube 112. The pressure respiration component 534 produces a pressure respiration signal. The pressure respiration component 534 includes a pressure transducer (not shown) for converting a pressure signal from the pressure sensor 100 to an electrical signal (pressure respiration signal). The pressure respiration component 534 provides the pressure respiration signal to a pressure respiration signal quality check component 535. The pressure respiration signal quality check component 535 runs a quality test on the pressure respiration signal.

The ECG respiration signal quality check component 533 and the pressure respiration signal quality check component 535 may use a variety of different techniques for artifact and/or noise detection. For example, and not by way of limitation, the ECG respiration signal quality check component 533 and the pressure respiration signal quality check component 535 may use one or more of the following methods: (1) the adaptive moving average filtering, variable length peak detection window, and comparison of detected peaks to an adaptive threshold to distinguish noise peaks from respiration signal peaks taught by R. Lukocius, J. A. Virbalis, J. Daunoras, and A. Vegys, "The Respiration Rate Estimation Method based on the Signal Maximums and Minimums Detection and the Signal Amplitude Evaluation," Electronics and Electrical Engineering, Kaunaus: Technologija, 2008, No. 8 (88), pp. 51-54; (2) the signal abnormality index algorithm taught by J. X. Sun, A. T. Reisner, and R. G. Mark, "A Signal Abnormality Index for Arterial Blood Pressure Waveforms," Computers in Cardiology, 2006, vol. 33, pp. 13-16; (3) the correlation algorithm taught by G. D. Clifford, A. Aboukhalil, J. X. Sun, W. Zong, B. A. Janz, G. B. Moody, and R. G. Mark, "Using the Blood Pressure Waveform to Reduce Critical False ECG Alarms," Computers in Cardiology, 2006, vol. 33, pp. 829-832; (4) the signal quality metrics taught by Q. Li, R. G. Mark, and G. D. Clifford, "Robust Heart Rate Estimation from Multiple Asynchronous Noisy Sources using Signal Quality Indices and a Kalman Filter," IOP Physiological Measurement, January 2008, 29(1), pp. 15-32; (5) the ECG artifact detection taught by J. A. Jiang, C. F. Chao, M. J. Chiu, and R. G. Lee, "An Automatic Analysis Method for Detecting and Eliminating ECG Artifacts in EEG," Computers in Biology and Medicine, November 2007, Vol. 37, Issue 11, pp. 1660-1671; and/or (6) the noise and artifact detection taught by dePinto in U.S. Pat. No. 5,983,127. Artisans will recognize from the disclosure herein that the noise and artifact detection in the physiological signals discussed in the references listed above may be applied to the respiration signals discussed herein. Further, artisans will recognize from the disclosure herein that the ECG respiration signal quality check component 533 and the pressure respiration signal quality check component 535 may use other known noise and/or artifact detection methods to determine the quality of the respective respiration signals.

The system 500 also includes respiration decision logic 536 to determine the patient's respiration rate based on one or both of the ECG respiration signal and the pressure respiration signal. The ECG respiration signal quality check component 533 provides the ECG respiration signal and an indication of the ECG respiration signal's quality to the respiration decision logic 536. Similarly, the pressure respiration signal quality check component 535 provides the pressure respiration signal and an indication of the pressure respiration signal's quality to the respiration decision logic 536.

Based on the respective indications of signal quality, the respiration decision logic 536 determines whether to use the ECG respiration signal, the pressure respiration signal, or a combination of the ECG respiration signal and the pressure respiration signal to determine the patient's respiration rate.

For example, the ECG respiration signal quality check component 533 may indicate that the ECG respiration signal is noisy or includes excessive artifacts, and the pressure respiration signal quality component check component 535 may indicate that the pressure respiration signal has an acceptable quality. In such a case, the respiration decision logic 536 is configured to use the pressure respiration signal to determine the patient's respiration rate. Similarly, if the ECG respiration signal has an acceptable quality and the pressure respiration signal has a poor quality, the respiration decision logic 536 uses the ECG respiration signal to determine the patient's respiration rate.

In one embodiment, if both the ECG respiration signal and the pressure respiration signal have an acceptable quality, then the respiration decision logic 536 may select either respiration signal to determine the patient's respiration rate. In another embodiment, if both respiration signals have an acceptable quality, then the respiration decision logic 536 may select the respiration signal with the highest quality to determine the patient's respiration rate. In another embodiment, if both the ECG respiration signal and the pressure respiration signal have an acceptable quality, both respiration signals may be used to determine the patient's respiration rate. For example, the respiration rates derived from both respiration signals may be averaged. In certain such embodiments, the respiration rates derived from both respiration signals are averaged if the difference between the two respiration rates are less than 10% to 15%. In one embodiment, if neither the ECG respiration signal nor the pressure respiration signal has an acceptable quality, then the patient's respiration rate is not determined and/or displayed until an acceptable respiration signal is acquired from either source.

The respiration decision logic 536 is connected to the bus 528 such that it may provide the derived respiration rate and/or the waveform 228 to the memory device 514, the interface component 516, and/or the display device 538. In one embodiment, the system 500 allows a clinician to select data corresponding to one or more of the leads for display as an ECG signal on a display device 538. The system 500 also allows a clinician to display the patient's respiration rate on the display device 538 and/or the waveform 232 representing the patient's respiration.

In certain embodiments, the system 500 also includes a respiration alarm 540 that compares the respiration rate produced by the respiration decision logic 536 to one or more respiration rate threshold condition. For example, a high respiration rate threshold and a low respiration rate threshold may be provided. If the derived respiration rate equals or exceeds the high respiration rate threshold, the respiration alarm 540 provides indicia of an alarm condition. Similarly, if the derived respiration rate equals or falls below the low respiration rate threshold, the respiration alarm 540 provides indicia of an alarm condition. To provide the alarm indicia, for example, the respiration alarm 540 may display an alarm symbol (not shown) on the display device 538 and/or provide an audible alarm.

The ECG component 530, the ECG respiration component 532, the pressure respiration component 534, and the respiration decision logic 536, may include a special purpose processor configured to perform the processes described herein. In another embodiment, these components may include a general purpose processor configured to execute computer executable instructions (e.g., stored in a computer-readable medium (such as the memory device 514) to perform the processes described herein. In addition or in other embodiments, these devices may be connected to a host computer (not shown) having a display device of its own. The host computer may include computer executable instructions for forming the processes described herein. Those computers may be used in certain embodiments, for example, to provide remote patient monitoring.

It will be understood by those having skill in the art that many changes may be made to the details of the above-described embodiments without departing from the underlying principles of the invention. The scope of the present invention should, therefore, be determined only by the following claims.

What is claimed is:

1. A patient monitoring system comprising:
   a plurality of electrocardiogram (ECG) lead channels configured to communicate with a plurality of ECG electrodes configured to attach to a patient;
   an ECG respiration component to produce a first respiration signal based on variations detected in the ECG lead channels;
   a pressure measurement channel to communicate with a pressure sensor attached to the patient;
   a pressure respiration component configured to detect variations in the pressure measurement channel and to produce a second respiration signal based on pressure variations detected in the pressure measurement channel;
   a first respiration signal quality check component to determine a first signal quality corresponding to the first respiration signal; and
   a second respiration signal quality check component to determine a second signal quality corresponding to the second respiration signal;
   respiration decision logic configured to compare the first signal quality to the second signal quality and to produce a respiration rate from at least one of the first respiration signal and the second respiration signal based on the comparison of the first signal quality and the second signal quality; and
   a display device to provide indicia of the respiration rate.

2. The system of claim 1, wherein the variations detected in the ECG lead channels comprise variations in thoracic impedance during patient respiration.

3. The system of claim 2, wherein the ECG respiration component is configured to:
   produce an impedance signal between two or more of the ECG electrodes; and
   produce the first respiration signal based on variations in the impedance signal.

4. The system of claim 1, wherein the ECG lead channels are configured to receive ECG signals related to electrical waves that cause the patient's heart muscle to pump, and wherein the variations detected in the ECG lead channels comprise variations in the ECG signals corresponding to patient respiration.

5. The system of claim 1, further comprising an ECG electrode to detect ECG signals related to electrical waves that cause the patient's heart muscle to pump, the ECG electrode configured and sized to temporarily secure the pressure sensor to the patient.

6. The system of claim 1, further comprising an integrated apparatus for measuring electrical signals and physical movements in the patient, the integrated apparatus comprising:
   a body comprising a top surface and a bottom surface;
   an electrically conductive adhesive covering at least a portion of the bottom surface to temporarily secure the integrated apparatus to the patient's skin;
   an electrically conductive lead attachment passing from the top surface to the bottom surface of the body to provide electrical communication between the patient's skin and one of the ECG lead channels;
   a pressure capsule secured below the top surface of the body, the pressure capsule responsive to changes in pressure applied thereto; and
   a pressure communication tube connected to the pressure capsule to communicate pressure variations within the pressure capsule to the pressure measurement channel.

7. The system of claim 6, wherein the integrated apparatus is disposable.

8. The system of claim 1, further comprising a respiration alarm to:
   compare the respiration rate produced by the respiration decision logic to a respiration rate threshold condition; and
   provide indicia of an alarm based on the comparison.

9. The system of claim 1, wherein the display device displays a numerical value of the respiration rate.

10. The system of claim 1, wherein the display device displays a waveform representing the sequence of times corresponding to the respiration rate.

11. A method for monitoring a respiration rate of a patient, the method comprising:
    attaching a plurality of electrocardiogram (ECG) electrodes and a pressure sensor to a patient;
    detecting variations in the plurality of ECG electrodes and producing a first respiration signal based on variations detected in signals provided by the ECG electrodes attached to the patient;
    detecting pressure variations in the pressure sensor and producing a second respiration signal based on pressure variations detected in the pressure sensor secured to the patient;
    determining a first signal quality corresponding to the first respiration signal;
    determining a second signal quality corresponding to the second respiration signal;
    comparing the first signal quality to the second signal quality and selecting at least one of the first respiration signal and the second respiration signal based on the comparison of the first signal quality and the second signal quality;
    producing a respiration rate from the selected signal; and
    providing indicia of the respiration rate.

12. The method of claim 11, wherein producing the first respiration signal comprises:
    producing an impedance signal between two or more of the ECG electrodes; and
    detecting variations in the impedance signal corresponding to patient respiration.

13. The method of claim 11, wherein producing the first respiration signal comprises:
    receiving ECG signals related to electrical waves that cause the patient's heart muscle to pump; and
    detecting variations in the ECG signals corresponding to patient respiration.

14. The method of claim 11, wherein attaching the plurality of ECG electrodes and the pressure sensor to the patient comprises applying an adhesive ECG electrode over the pressure sensor to temporarily secure the ECG electrode the patient's skin, wherein the ECG electrode provides an electrical connection to the patient's skin.

15. The method of claim 11, wherein the pressure sensor is integrated into one of the plurality of ECG electrodes, and wherein attaching the plurality of ECG electrodes and the pressure sensor to the patient comprises attaching the integrated ECG electrode and pressure sensor to the patient's abdomen or chest.

16. The method of claim 11, wherein selecting at least one of the first respiration signal and the second respiration signal comprises:
selecting the highest quality among the first signal quality and the second signal quality.

17. The method of claim 11, wherein selecting at least one of the first respiration signal and the second respiration signal comprises:
determining that at both the first signal quality and the second signal quality are at an acceptable level; and
based on the determination, randomly selecting either the first respiration signal or the second respiration signal.

18. The method of claim 11, wherein selecting at least one of the first respiration signal and the second respiration signal comprises:
determining that both the first signal quality and the second signal quality are at an acceptable level;
determining a first respiration rate from the first respiration signal;
determining a second respiration rate from the second respiration signal; and
averaging the first respiration rate and the second respiration rate.

19. The method of claim 11, further comprising:
comparing the respiration rate to a respiration rate threshold condition; and
providing indicia of an alarm based on the comparison.

20. The method of claim 11, wherein providing the indicia comprises numerically displaying the respiration rate on a display device of a patient monitor.

21. The method of claim 11, wherein providing the indicia comprises displaying a graphical waveform representing the sequence of times corresponding to the respiration rate on a display device of a patient monitor.

22. A patient monitor comprising:
means for detecting variations in a plurality of ECG electrodes configured to attach to a patient and producing a first respiration signal based on variations detected in the ECG electrodes configured to attach to a patient;
means for detecting variations in a pressure sensor configured to attach to a patient and producing a second respiration signal based on pressure variations detected in the pressure sensor configured to attach to the patient;
means for determining a first signal quality corresponding to the first respiration signal; and
means for determining a second signal quality corresponding to the second respiration signal;
means for comparing the first signal quality to the second signal quality and selecting at least one of the first respiration signal and the second respiration signal based on the comparison of the first signal quality and the second signal quality;
means for producing a respiration rate from the selected signal; and
means for providing indicia of the respiration rate.

* * * * *